United States Patent
Yasuda et al.

(10) Patent No.: US 8,354,644 B2
(45) Date of Patent: Jan. 15, 2013

(54) TOTAL REFLECTION TERA HERTZ WAVE MEASURING APPARATUS

(75) Inventors: Takashi Yasuda, Hamamatsu (JP);
Yoichi Kawada, Hamamatsu (JP);
Hironori Takahashi, Hamamatsu (JP);
Shinichiro Aoshima, Hamamatsu (JP);
Atsuko Aoshima, legal representative, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 548 days.

(21) Appl. No.: 12/530,897

(22) PCT Filed: Feb. 13, 2008

(86) PCT No.: PCT/JP2008/052336
§ 371 (c)(1),
(2), (4) Date: Dec. 22, 2009

(87) PCT Pub. No.: WO2008/111351
PCT Pub. Date: Sep. 18, 2008

(65) Prior Publication Data
US 2010/0091266 A1    Apr. 15, 2010

(30) Foreign Application Priority Data
Mar. 13, 2007  (JP) .................. P2007-063878

(51) Int. Cl.
*G01J 5/02*    (2006.01)
(52) U.S. Cl. .................................... 250/341.1
(58) Field of Classification Search ............... 250/341.1
See application file for complete search history.

(56) References Cited

U.S. PATENT DOCUMENTS
6,366,411 B1 * 4/2002 Kimura et al. ............. 359/729
(Continued)

FOREIGN PATENT DOCUMENTS
JP    2000-348367    12/2000
(Continued)

OTHER PUBLICATIONS

Hideki Hirori et al., "Attenuated Total Reflection Spectroscopy in Time Domain Using Terahertz Coherent Pulses," Japanese Journal of Applied Physics, 2004, pp. L1287-L1289, vol. 43, No. 10A.
(Continued)

*Primary Examiner* — David Porta
*Assistant Examiner* — Mindy Vu
(74) *Attorney, Agent, or Firm* — Drinker Biddle & Reath LLP

(57) ABSTRACT

A total reflection terahertz wave measuring apparatus 1 is configured to acquire information on a subject S by a total reflection measurement method by use of a terahertz wave, and includes a light source 11, a branching part 12, a chopper 13, an optical path length difference adjusting part 14, a polarizer 15, a separator 17, a terahertz wave generating element 20, an internal total reflection prism 31, a terahertz wave detecting element 40, a ¼ wavelength plate 51, a polarization split element 52, a photodetector 53A, a photodetector 53B, a differential amplifier 54, and a lock-in amplifier 55. The internal total reflection prism 31 is a so-called aplanatic prism, and has an entrance plane 31a, an exit plane 31b, and a reflection plane 31c. The terahertz wave generating element 20 is provided to be integrated with the entrance plane 31a of the internal total reflection prism 31, and the terahertz wave detecting element 40 is provided to be integrated with the exit plane 31b of the internal total reflection prism 31.

6 Claims, 14 Drawing Sheets

U.S. PATENT DOCUMENTS

| | | | |
|---|---|---|---|
| 7,564,034 B2 * | 7/2009 | Ouchi | 250/340 |
| 2005/0179905 A1 * | 8/2005 | Ohtake et al. | 356/450 |
| 2006/0231762 A1 * | 10/2006 | Ohtake et al. | 250/341.8 |

FOREIGN PATENT DOCUMENTS

| | | |
|---|---|---|
| JP | 2004-354246 | 12/2004 |
| JP | 2006-184078 | 7/2006 |
| WO | WO 2006/070852 A1 * | 7/2006 |

OTHER PUBLICATIONS

Hideki Hirori et al., "Destructive interference effect on surface plasmon resonance in terahertz attenuated total reflection," Optics Express, Dec. 26, 2005, pp. 10801-10814, vol. 13, No. 26.

* cited by examiner (a)

34A (b)

34C     34B     34D (c)

34C     34B     34D

TOTAL REFLECTION TERA HERTZ WAVE MEASURING APPARATUS

TECHNICAL FIELD

The present invention relates to a total reflection terahertz wave measuring apparatus.

BACKGROUND ART

A terahertz wave is an electromagnetic wave having a frequency of approximately 0.01 THz to 100 THz corresponding to an intermediate range between light waves and radio waves, and has an intermediate property between light waves and radio waves. As an application of such a terahertz wave, a technology for acquiring information on a subject by measuring a temporal waveform of an electric field amplitude of a terahertz wave which is transmitted through or is reflected by the subject has been studied (refer to Patent Document 1).

A technology for measuring information on a subject by use of a terahertz wave is generally as follows. That is, a pulsed light output from a light source (for example, a femtosecond laser light source) is branched into two to be a pump light and a probe light by a branching part. The pump light between those is received by a terahertz wave generating element (for example, a nonlinear optical crystal or a photoconductive antenna element), and thereby, a pulsed terahertz wave is generated from the terahertz wave generating element. This generated terahertz wave is transmitted through or reflected by a subject, to acquire information (for example, an absorption coefficient, a refractive index) on the subject, and thereafter, the terahertz wave is made incident on a terahertz wave detecting element (for example, an electro-optic crystal or a photoconductive antenna element) in substantially the same timing as that of the probe light.

In the terahertz wave detecting element which receives the terahertz wave and the probe light, a correlation between both lights is detected. For example, in a case in which an electro-optic crystal is used as the terahertz wave detecting element, the terahertz wave and the probe light are coupled by a wave synthesizer, to be made incident on the electro-optic crystal, and birefringence is induced in accordance with propagation of the terahertz wave in the electro-optic crystal, and a polarization state of the probe light is changed by the birefringence. A change in the polarization state of the probe light in the electro-optic crystal is detected. As a result, an electric field amplitude of the terahertz wave is detected, which enables to acquire information on the subject.

With respect to acquisition of information on a subject with a terahertz wave, as disclosed in Patent Document 1, in some cases, acquisition of information on a subject with a terahertz wave is carried out, not only by transmission or reflection of a terahertz wave through or by a subject part, but also by making a terahertz wave be totally reflected by a plane of a prism to generate an evanescent component, and to irradiate the subject on the plane with the evanescent component of the terahertz wave. According to the description in Patent Document 1, the technology by utilizing total reflection of a terahertz wave yields advantageous effects that a subject is not limited to a solid substance and the like.

Patent Document 1: Japanese Published Unexamined Patent Application No. 2004-354246
Patent Document 2: Japanese Published Unexamined Patent Application No. 2006-184078

DISCLOSURE OF THE INVENTION

Problem to be Solved by the Invention

However, in a conventional art, the number of components included in an optical system from a light source up to a terahertz wave detecting element is large, which results in a large-sized apparatus. Further, because a terahertz wave is absorbed by water included in a space in which a terahertz wave is propagated, it is necessary to conduct a nitrogen purge in this space, and from this standpoint as well, the apparatus is made large-sized.

The present invention has been achieved in order to solve the above-described problems, and an object of the present invention is to provide a total reflection terahertz wave measuring apparatus which can be downsized.

Means for Solving the Problem

A total reflection terahertz wave measuring apparatus according to the present invention includes (1) a light source for outputting light, (2) a branching part for branching the light output from the light source into two, to output one of the lights branched into two as a pump light and the other one as a probe light, (3) a terahertz wave generating element for generating and outputting a terahertz wave by receiving the pump light output from the branching part, (4) an internal total reflection prism for receiving the terahertz wave output from the terahertz wave generating element to an entrance plane, making the received terahertz wave be propagated internally to be totally reflected by a reflection plane, and outputting the terahertz wave from an exit plane to the outside, and (5) a terahertz wave detecting element for receiving the terahertz wave output from the exit plane of the internal total reflection prism and the probe light output from the branching part, to detect a correlation between the terahertz wave and the probe light. Moreover, in the total reflection terahertz wave measuring apparatus according to the present invention, the terahertz wave generating element is provided to be integrated with the entrance plane of the internal total reflection prism, the terahertz wave detecting element is provided to be integrated with the exit plane of the internal total reflection prism, and information on a subject disposed on the reflection plane of the internal total reflection prism is acquired with an evanescent component of the terahertz wave generated at the time of total reflection of the terahertz wave.

In the total reflection terahertz wave measuring apparatus, the light output from the light source is branched into two by the branching part, to be output as a pump light and a probe light. The pump light output from the branching part is received by the terahertz wave generating element, and a terahertz wave is generated by the terahertz wave generating element to be output. The terahertz wave output from the terahertz wave generating element is, not propagated in a space, but directly received by the entrance plane of the internal total reflection prism, and is propagated inside the internal total reflection prism to be totally reflected by the reflection plane, and is output from the exit plane of the internal total reflection prism to the outside. The terahertz wave output from the exit plane of the internal total reflection prism is, not propagated in a space, but directly received by the terahertz wave detecting element. The terahertz wave output from the exit plane of the internal total reflection prism and the probe light output from the branching part are received by the terahertz wave detecting element, and a correlation between the terahertz wave and the probe light is detected by the terahertz wave detecting element. At this time, information on the subject disposed on the reflection plane of the internal total reflection prism is acquired with an evanescent component of the terahertz wave generated at the time of total reflection of a terahertz wave.

The total reflection terahertz wave measuring apparatus preferably further includes an optical path length difference adjusting part for adjusting a difference between an optical path of the pump light and the terahertz wave from the branching part up to the terahertz wave detecting element and an optical path of the probe light from the branching part up to the terahertz wave detecting element. In this case, the terahertz wave and the probe light are respectively adjusted in timing of being received by the terahertz wave detecting element by the optical path length difference adjusting part, and by sweeping the timing, a temporal waveform of an electric field amplitude of the pulsed terahertz wave can be acquired. Note that the optical path length difference adjusting part may be provided to any one of the pump light optical system, the probe light optical system, and the terahertz wave optical system.

In the total reflection terahertz wave measuring apparatus, an optical element for yielding a collimation effect on a terahertz wave propagated inside the internal total reflection prism is preferably formed at a side of the entrance plane of the internal total reflection prism. Further, in the total reflection terahertz wave measuring apparatus, an optical element for yielding a light-condensing effect on a terahertz wave propagated inside the internal total reflection prism is preferably formed at a side of the exit plane of the internal total reflection prism. In this way, provided that an optical element (for example, a lens or an off-axis paraboloidal mirror) yielding a collimation effect or a light-condensing effect is formed to the internal total reflection prism, it is advantageous to a case in which the terahertz wave generating element or the terahertz wave detecting element is a photoconductive antenna element.

In the total reflection terahertz wave measuring apparatus, the internal total reflection prism preferably has, in addition to the entrance plane, the reflection plane, and the exit plane, a first secondary reflection plane for reflecting the terahertz wave received by the entrance plane to be propagated internally toward the reflection plane, and a second secondary reflection plane for reflecting the terahertz wave reflected by the reflection plane to be propagated internally toward the exit plane. Further, in the total reflection terahertz wave measuring apparatus, a principal ray of the terahertz wave received by the entrance plane of the internal total reflection prism and a principal ray of the terahertz wave output from the exit plane of the internal total reflection prism are preferably on a common straight line. Such an internal total reflection prism is realized by, for example, an aplanatic prism.

Effect of the Invention

The total reflection terahertz wave measuring apparatus according to the present invention can be downsized.

Figure 1:
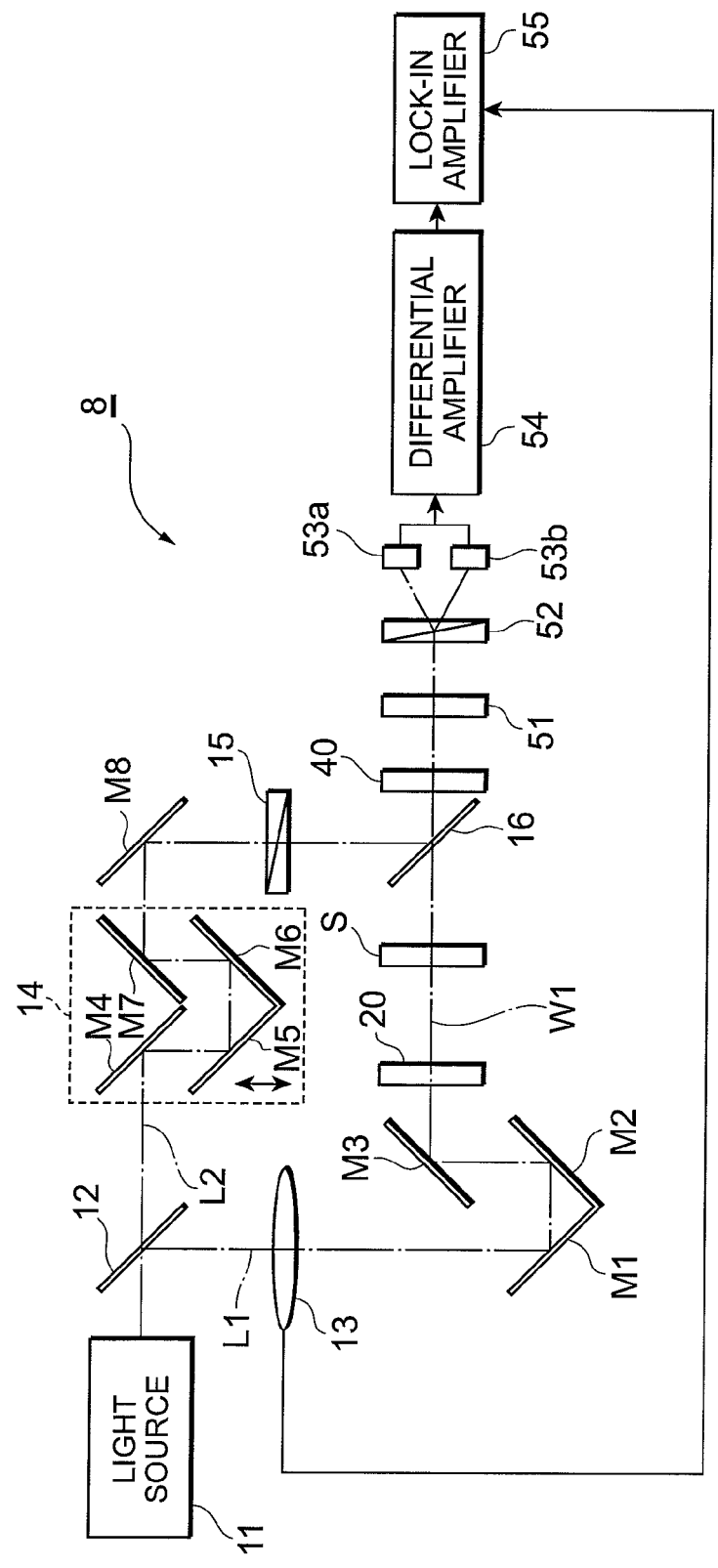
FIG. 1 is a diagram showing the configuration of a terahertz wave measuring apparatus 8 according to the first comparative example.

DESCRIPTION OF SYMBOLS 1 to 3 . . . total reflection terahertz wave measuring apparatus, 11 . . . light source, 12 . . . branching part, 13 . . . chopper, 14 . . . optical path length difference adjusting part, 15 . . . polarizer, 16 . . . wave synthesizer, 17 . . . separator, 20, 21 . . . terahertz wave generating element, 31 to 35 . . . internal total reflection prism, 40, 41 . . . terahertz wave detecting element, 51 . . . ¼ wavelength plate, 52 . . . polarization split element, 53A, 53B photodetector, 54 . . . differential amplifier, 55 . . . lock-in amplifier, 56 . . . signal generating part, 57 . . . synchronous detection part, M1 to M9 . . . mirror, S . . . subject.

BEST MODES FOR CARRYING OUT THE INVENTION

Hereinafter, a best mode for carrying out the present invention will be described in detail with reference to the accompanying drawings. In the descriptions of the drawings, components identical or equivalent to each other are attached with the same reference characters, and overlapping description is omitted. Further, configurations according to a first comparative example and a second comparative example to be compared with a configuration of an embodiment of the present invention will be first described. Thereafter, the configuration of the embodiment will be described in comparison with the configurations of these comparative examples.

FIRST COMPARATIVE EXAMPLE

First, a terahertz wave measuring apparatus 8 according to the first comparative example will be described. FIG. 1 is a diagram showing the configuration of the terahertz wave measuring apparatus 8 according to the first comparative example. The terahertz wave measuring apparatus 8 shown in the drawing is configured to acquire information on a subject S by a transmission measurement method by use of a terahertz wave, and the terahertz wave measuring apparatus 8 includes a light source 11, a branching part 12, a chopper 13, an optical path length difference adjusting part 14, a polarizer 15, a wave synthesizer 16, a terahertz wave generating element 20, a terahertz wave detecting element 40, a ¼ wavelength plate 51, a polarization split element 52, a photodetector 53A, a photodetector 53B, a differential amplifier 54, and a lock-in amplifier 55.

The light source 11 is to output a pulsed light at a constant cycle period, and is preferably a femtosecond pulsed laser light source for outputting a pulsed laser light whose pulse duration is approximately femtoseconds. The branching part 12 is, for example, a separator, and branches a pulsed light output from the light source 11 into two, and outputs one of the pulsed lights branched into two to a mirror M1 as a pump light L1, and outputs the other one to a mirror M4 as a probe light L2.

The chopper 13 is provided on an optical path of the pump light L1 between the branching part 12 and the mirror M1, to repeat alternately transmitting and blocking the pump light L1 at a constant period. The pump light L1 output from the branching part 12 to pass through the chopper 13 is sequentially reflected by mirrors M1 to M3, to be received by the terahertz wave generating element 20. Note that the optical system for the pump light L1 from the branching part 12 up to the terahertz wave generating element 20 is hereinafter called "pump optical system."

The terahertz wave generating element 20 is to generate and output a pulsed terahertz wave W1 by receiving the pump light L1, and is, for example, formed so as to include any one of a nonlinear optical crystal (for example, ZnTe), a photoconductive antenna element (for example, an optical switch using GaAs), a semiconductor (for example, InAs), and a superconductive conductor. In a case in which the terahertz wave generating element 20 includes a nonlinear optical crystal, the terahertz wave generating element 20 is capable of generating a terahertz wave due to a nonlinear optical phenomenon arising according to a pump light incidence.

A terahertz wave is an electromagnetic wave having a frequency of approximately 0.01 THz to 100 THz corresponding to an intermediate range between light waves and radio waves, and has an intermediate property between light waves and radio waves. Further, a pulsed terahertz wave is generated at a constant cycle period, and its pulse duration is approximately several picoseconds. The terahertz wave W1 output from the terahertz wave generating element 20 is transmitted through the subject S to acquire information on the subject S (for example, an absorption coefficient, a refractive index), and thereafter, the terahertz wave W1 is received by the wave synthesizer 16. Note that the optical system for the terahertz wave W1 from the terahertz wave generating element 20 up to the wave synthesizer 16 is hereinafter called "terahertz wave optical system."

On the other hand, the probe light L2 output from the branching part 12 is sequentially reflected by mirrors M4 to M8, and passes through the polarizer 15 to be received by the wave synthesizer 16. Note that the optical system for the probe light L2 from the branching part 12 up to the wave synthesizer 16 is hereinafter called "probe optical system." The four mirrors M4 to M7 compose the optical path length difference adjusting part 14. That is, an optical path length between the mirrors M4 and M7 and the mirrors M5 and M6 is adjusted by moving the mirrors M5 and M6, to adjust an optical path length of the probe optical system. Thereby, the optical path length difference adjusting part 14 is capable of adjusting a difference between an optical path of the pump optical system and the terahertz wave optical system from the branching part 12 up to the wave synthesizer 16 and an optical path of the probe optical system from the branching part 12 up to the wave synthesizer 16.

The terahertz wave output from the terahertz wave generating element 20 to be transmitted through the subject S and the probe light output from the branching part 12 to reach the wave synthesizer 16 are received by the wave synthesizer 16, and the wave synthesizer 16 couples these terahertz wave and probe light so as to be coaxial with each other, and outputs those to the terahertz wave detecting element 40. The wave synthesizer 16 is preferably a pellicle that is a film type mirror, which is bonded to a solid base frame so as to be stretched to be thin.

The terahertz wave detecting element 40 is to detect a correlation between a terahertz wave and a probe light. In a case in which the terahertz wave detecting element 40 includes an electro-optic crystal, the terahertz wave detecting element 40 receives the terahertz wave and the probe light output from the wave synthesizer 16, induces birefringence due to a Pockels effect in accordance with propagation of the terahertz wave, changes a polarization state of the probe light by the birefringence, and outputs the changed probe light. Because an amount of birefringence at this time is dependent on an electric field intensity of the terahertz wave, an amount of change in a polarization state of the probe light in the terahertz wave detecting element 40 is dependent on an electric field intensity of the terahertz wave.

The polarization split element 52 is, for example, a Wollaston prism, and receives the probe light output from the terahertz wave detecting element 40 through the ¼ wavelength plate 51, and the polarization split element 52 splits the received probe light into two polarization components perpendicular to one another, and outputs those. The photodetectors 53A and 53B include, for example, photodiodes, and detect powers of the two polarization components of the probe light split to be polarized by the polarization split element 52, to output electric signals having values corresponding to the detected powers to the differential amplifier 54.

The differential amplifier 54 receives the electric signals respectively output from the photodetectors 53A and 53B and outputs an electric signal having a value corresponding to a difference between the values of both electric signals to the lock-in amplifier 55. The lock-in amplifier 55 synchronously detects the electric signal output from the differential amplifier 54 at a repetition frequency for transmitting and blocking the pump light L1 by the chopper 13. The signal output from the lock-in amplifier 55 has a value dependent on an electric field intensity of the terahertz wave. In this way, it is possible to detect a correlation between the probe light and the terahertz wave which are transmitted through the subject S, detect an electric field amplitude of the terahertz wave, and thereby acquire information on the subject S.

The terahertz wave measuring apparatus 8 operates as follows. A pulsed light output from the light source 11 is branched into two to be the pump light L1 and the probe light L2 by the branching part 12. The pump light L1 output from the branching part 12 is sequentially reflected by the mirrors M1 to M3, to be received by the terahertz wave generating element 20. The terahertz wave generating element 20 generates and outputs the terahertz wave W1 in accordance with receiving the pump light L1. The terahertz wave W1 output from the terahertz wave generating element 20 is transmitted through the subject S to be received by the wave synthesizer 16. On the other hand, the probe light L2 output from the branching part 12 is sequentially reflected by the mirrors M4 to M8, and is made into a linearly-polarized light by the polarizer 15 to be received by the wave synthesizer 16.

The terahertz wave and the probe light received by the wave synthesizer 16 are coupled so as to be coaxial with each other by the wave synthesizer 16, and those are received by the terahertz wave detecting element 40 in substantially the same timing. In the terahertz wave detecting element 40 which receives the terahertz wave and the probe light, birefringence is induced in accordance with propagation of the terahertz wave, and a polarization state of the probe light is changed by the birefringence. Then, the polarization state of the probe light in the terahertz wave detecting element 40 is detected by the ¼ wavelength plate 51, the polarization split element 52, the photodetector 53A, the photodetector 53B, the differential amplifier 54, and the lock-in amplifier 55. In this way, a change in the polarization state of the probe light in the terahertz wave detecting element 40 is detected. As a result, an electric field amplitude of the terahertz wave is detected, which enables to acquire characteristics on the subject S.

However, in such a transmission measurement method, because a terahertz wave is greatly absorbed by water, the subject S is normally limited to a dry solid substance. A total reflection terahertz wave measuring apparatus 9 according to the second comparative example, which will be described next, is capable of solving such a problem.

SECOND COMPARATIVE EXAMPLE

Figure 2:
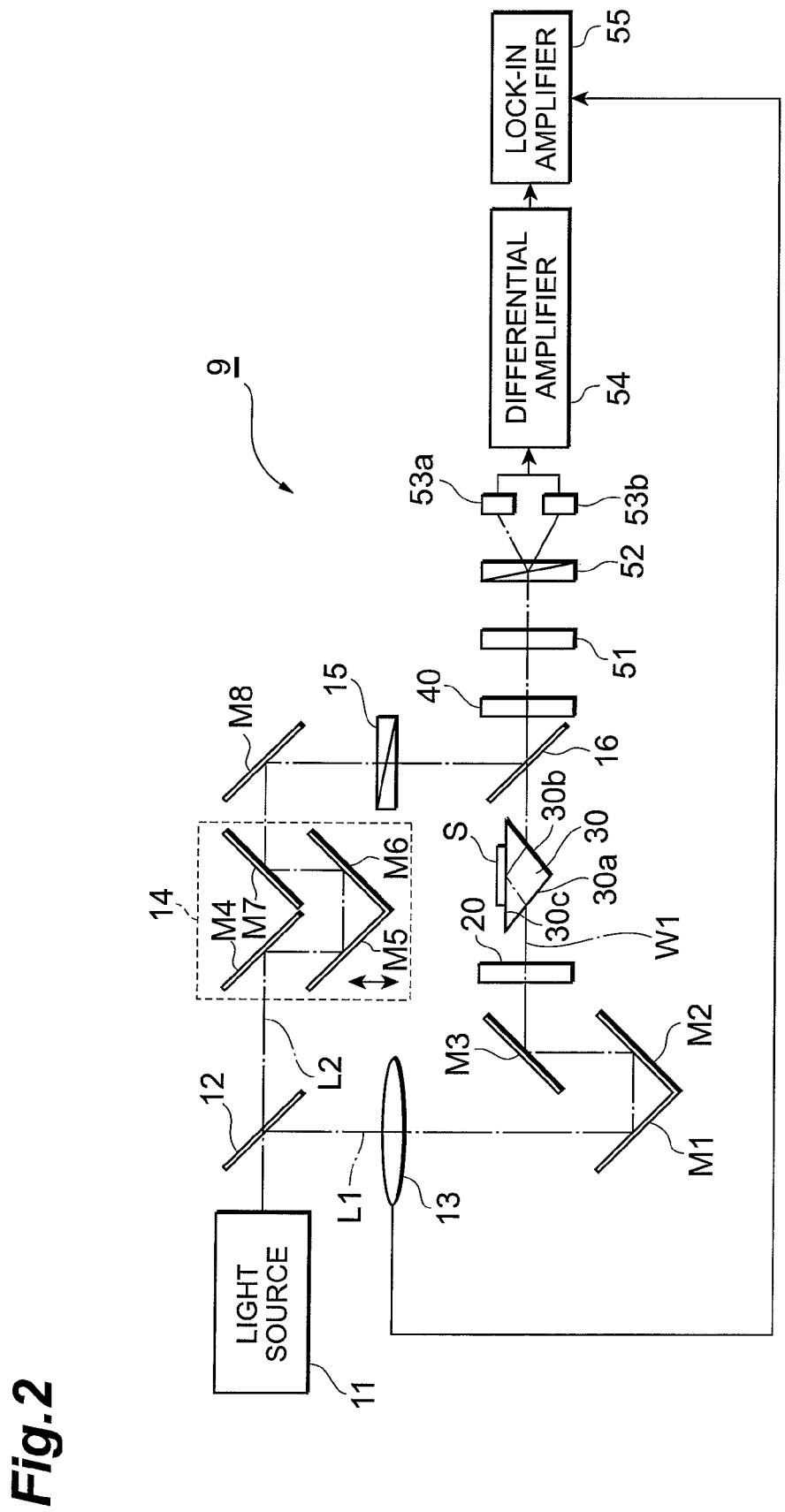
FIG. 2 is a diagram showing the configuration of a total reflection terahertz wave measuring apparatus 9 according to the second comparative example.

Next, a total reflection terahertz wave measuring apparatus 9 according to the second comparative example will be described. FIG. 2 is a diagram showing the configuration of the total reflection terahertz wave measuring apparatus 9 according to the second comparative example. The total reflection terahertz wave measuring apparatus 9 shown in the drawing is configured to acquire information on the subject S by a total reflection measurement method by use of a terahertz wave, and the total reflection terahertz wave measuring apparatus 9 includes the light source 11, the branching part 12, the chopper 13, the optical path length difference adjusting part 14, the polarizer 15, the wave synthesizer 16, the terahertz wave generating element 20, a prism 30, the terahertz wave detecting element 40, the ¼ wavelength plate 51, the polarization split element 52, the photodetector 53A, the photodetector 53B, the differential amplifier 54, and the lock-in amplifier 55.

As compared with the configuration of the terahertz wave measuring apparatus 8 according to the first comparative example shown in FIG. 1, the total reflection terahertz wave measuring apparatus 9 according to the second comparative example shown in FIG. 2 is different in the point that the apparatus includes the prism 30 on its terahertz wave optical system. The prism 30 receives the terahertz wave W1 output from the terahertz wave generating element 20 on an entrance plane 30a, and makes the received terahertz wave be propagated internally to be totally reflected by a reflection plane 30c, and outputs the totally-reflected terahertz wave from an exit plane 30b to the wave synthesizer 16. The prism 30 is a Dachkantoprisma, and a principal ray of the terahertz wave received on the entrance plane 30a and a principal ray of the terahertz wave output from the exit plane 30b are on a common straight line. The subject S is disposed on the reflection plane 30c of the prism 30.

In the terahertz wave measuring apparatus 9, the terahertz wave W1 output from the terahertz wave generating element 20 is received by the entrance plane 30a of the prism 30, and is propagated inside the prism 30 to be totally reflected by the reflection plane 30c of the prism 30. At the time of the total reflection, an evanescent component of the terahertz wave exists on a portion adjacent to the reflection plane 30c, of the subject S. For this reason, the terahertz wave which has been totally reflected by the reflection plane 30c of the prism 30 acquires information on the portion adjacent to the reflection plane 30c, of the subject S. Then, the totally-reflected terahertz wave is propagated inside the prism 30 to be output from the exit plane 30b of the prism 30 to the outside. The terahertz wave output from the prism 30 is received along with the probe light going through the probe optical system by the wave synthesizer 16.

The terahertz wave and the probe light received by the wave synthesizer 16 are coupled so as to be coaxial with each other by the wave synthesizer 16, and are received by the terahertz wave detecting element 40 in substantially the same timing. In the terahertz wave detecting element 40 which receives the terahertz wave and the probe light, birefringence is induced in accordance with propagation of the terahertz wave, and a polarization state of the probe light is changed by the birefringence. Then, the polarization state of the probe light in the terahertz wave detecting element 40 is detected by the ¼ wavelength plate 51, the polarization split element 52, the photodetector 53A, the photodetector 53B, the differential amplifier 54, and the lock-in amplifier 55. In this way, the change in the polarization state of the probe light in the terahertz wave detecting element 40 is detected. As a result, an electric field amplitude of the terahertz wave is detected, which enables to acquire characteristics on the subject S.

In such a total reflection measurement method, even if the subject S disposed on the reflection plane 30c of the prism 30 contains moisture, measurement is possible. However, it is preferable that there is no or little moisture in the space in which the terahertz wave is propagated from the terahertz wave generating element 20 to the terahertz wave detecting element 40, and therefore, a nitrogen purge is needed for the space. The total reflection terahertz wave measuring apparatus according to the present embodiment, which will be described hereinafter, is capable of solving such a problem.

FIRST EMBODIMENT

Figure 3:
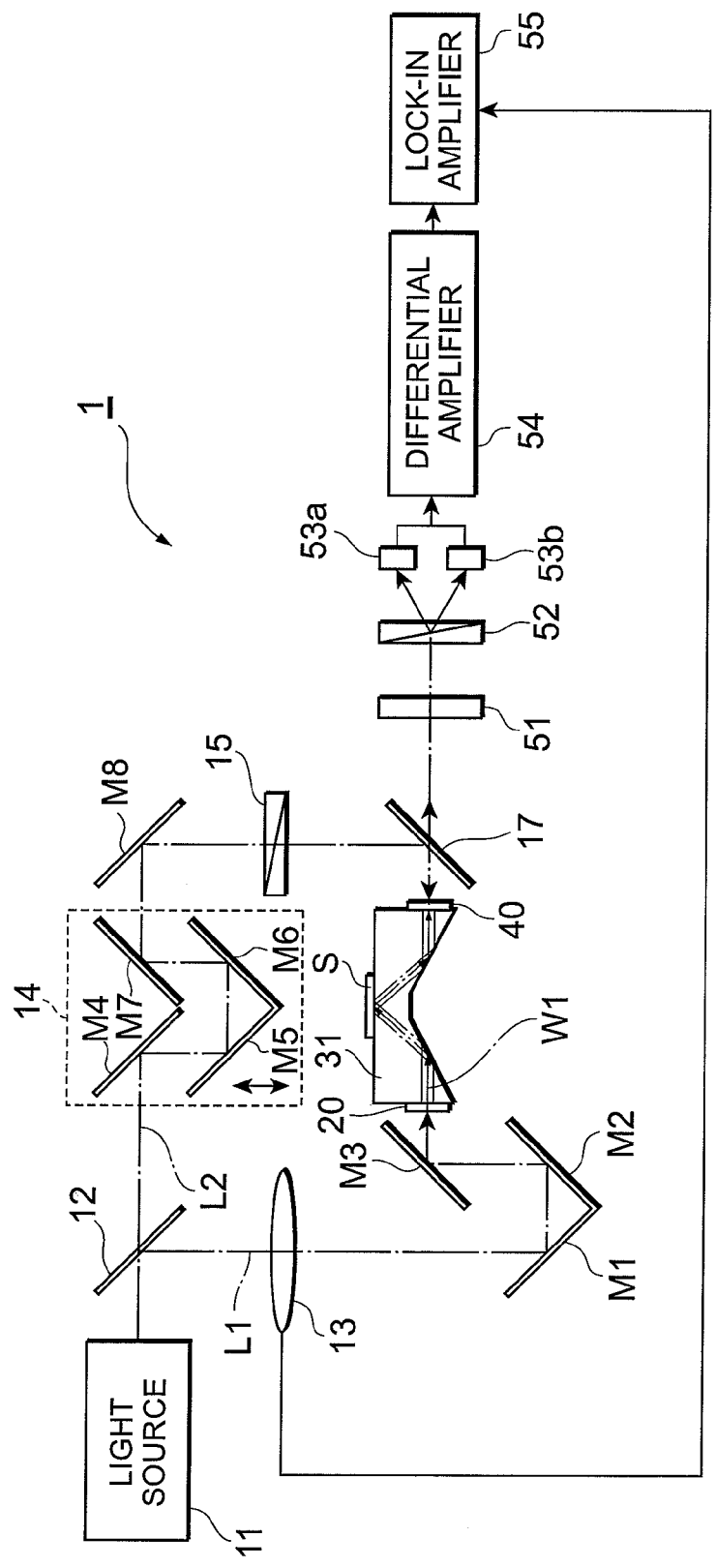
FIG. 3 is a diagram showing the configuration of a total reflection terahertz wave measuring apparatus 1 according to the first embodiment.

Next, a total reflection terahertz wave measuring apparatus 1 according to a first embodiment of the present invention will be described. FIG. 3 is a diagram showing the configuration of the total reflection terahertz wave measuring apparatus 1 according to the first embodiment. The total reflection terahertz wave measuring apparatus 1 shown in the drawing is configured to acquire information on the subject S by a total reflection measurement method by use of a terahertz wave, and the total reflection terahertz wave measuring apparatus 1 includes the light source 11, the branching part 12, the chopper 13, the optical path length difference adjusting part 14, the polarizer 15, a separator 17, the terahertz wave generating element 20, an internal total reflection prism 31, the terahertz wave detecting element 40, the ¼ wavelength plate 51, the polarization split element 52, the photodetector 53A, the photodetector 53B, the differential amplifier 54, and the lock-in amplifier 55.

As compared with the configuration of the total reflection terahertz wave measuring apparatus 9 according to the second comparative example shown in FIG. 2, the total reflection terahertz wave measuring apparatus 1 according to the first embodiment shown in FIG. 3 is different in the point that the apparatus includes the internal total reflection prism 31 in place of the prism 30, in the point that the terahertz wave generating element 20 and the terahertz wave detecting element 40 are provided to be integrated with the internal total reflection prism 31, and in the point that the apparatus includes the separator 17 in place of the wave synthesizer 16. Note that the separator 17 may be a pellicle.

Figure 4:
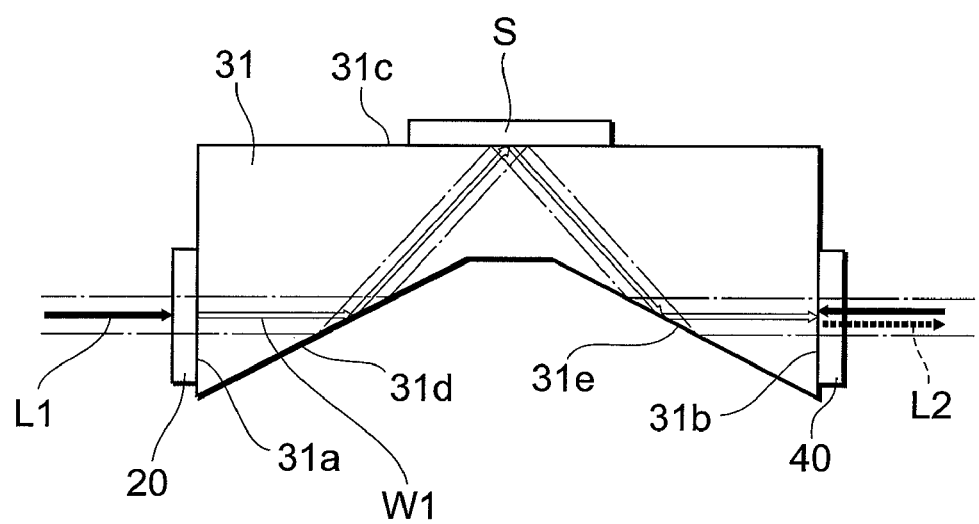
FIG. 4 is a cross sectional view of an internal total reflection prism 31 with which a terahertz wave generating element 20 and a terahertz wave detecting element 40 are provided to be integrated.
Figure 5:
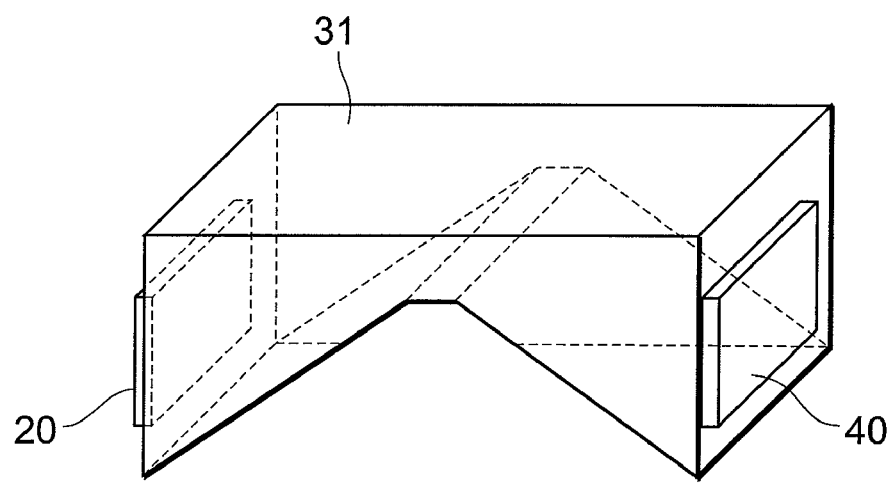
FIG. 5 is a perspective view of the internal total reflection prism 31 with which the terahertz wave generating element 20 and the terahertz wave detecting element 40 are provided to be integrated.

FIG. 4 is a cross sectional view of the internal total reflection prism 31 with which the terahertz wave generating element 20 and the terahertz wave detecting element 40 are provided to be integrated, and FIG. 5 is a perspective view of the internal total reflection prism 31. The internal total reflection prism 31 is a so-called aplanatic prism, and has an entrance plane 31a, an exit plane 31b, a reflection plane 31c, a first secondary reflection plane 31d, and a second secondary reflection plane 31e. The entrance plane 31a and the exit plane 31b are parallel to one another. The reflection plane 31c is perpendicular to the entrance plane 31a and the exit plane 31b. The terahertz wave generating element 20 is provided to be integrated with the entrance plane 31a of the internal total reflection prism 31, and the terahertz wave detecting element 40 is provided to be integrated with the exit plane 31b of the internal total reflection prism 31.

A principal ray of the terahertz wave W1 output from the terahertz wave generating element 20 to be received by the entrance plane 31a of the internal total reflection prism 31 is vertical to the entrance plane 31a, and a principal ray of the terahertz wave W1 output from the exit plane 31b of the internal total reflection prism 31 to be received by the terahertz wave detecting element 20 is vertical to the exit plane 31b, and the respective principal rays of these received terahertz wave and output terahertz wave are on a common straight line.

The internal total reflection prism 31 is composed of a material which is transmissive for a wavelength of the terahertz wave output from the terahertz wave generating element 20 and has a refractive index higher than that of the subject S disposed on the reflection plane 31c, and is preferably composed of silicon, for example. Silicon is transmissive in a waveband of a terahertz wave, and its refractive index is 3.4 at a wavelength of 1 THz. Further, for example, assuming that the principal component of the subject S is water, its refractive index is 2.0 at a water wavelength of 1 THz. At this time, because a critical angle is 36 degrees ($=\sin^{-1}(2.0/3.4)$), total reflection is brought about when an angle of incidence is greater than the critical angle. In a case in which the subject S is a gas as well, total reflection is brought about in the same way.

When the terahertz wave generating element 20 and the terahertz wave detecting element 40 are integrated with the internal total reflection prism 31, the terahertz wave generating element 20 is connected to the entrance plane 31a of the internal total reflection prism 31 with an adhesive, and the terahertz wave detecting element 40 is connected to the exit plane 31b of the internal total reflection prism 31 with an adhesive. The adhesives used at this time are preferably transmissive for a wavelength of a terahertz wave, and preferably have refractive indexes which are intermediate between respective refractive indexes of the terahertz wave generating element 20 and the terahertz wave detecting element 40 and a refractive index of the internal total reflection prism 31, or the same as those.

Further, the adhesive at the connecting position between the reflection plane 31b of the internal total reflection prism 31 and the terahertz wave detecting element 40 preferably has a high reflectance for a wavelength of a probe light. A dielectric multilayer may be formed on the reflection plane 31b, and thereby, the reflection plane 31b is transmissive for a terahertz wave, and has a high reflectance for a wavelength of a probe light.

The internal total reflection prism 31 directly receives the terahertz wave W1 output from the terahertz wave generating element 20 on the entrance plane 31a, and allows the received terahertz wave W1 to be propagated internally, to be reflected by the first secondary reflection plane 31d, and to be incident on the reflection plane 31c. Further, the internal total reflection prism 31 totally reflects the terahertz wave W1 made incident on the reflection plane 31c by the reflection plane 31c, makes the totally-reflected terahertz wave be propagated internally to be reflected by the second secondary reflection plane 31e, and outputs the terahertz wave from the exit plane 31b to be directly received by the terahertz wave detecting element 40.

The total reflection terahertz wave measuring apparatus 1 operates as follows. A pulsed light output from the light source 11 is branched into two to be the pump light L1 and the probe light L2 by the branching part 12. The pump light L1 output from the branching part 12 is sequentially reflected by the mirrors M1 to M3, to be received by the terahertz wave generating element 20 provided so as to be integrated with the entrance plane 31a of the internal total reflection prism 31. In the terahertz wave generating element 20, the terahertz wave W1 is generated in accordance with receiving the pump light L1, to be output. The terahertz wave W1 output from the terahertz wave generating element 20 is, not propagated in a space, but directly received by the entrance plane 31a of the internal total reflection prism 31, to be propagated inside the internal total reflection prism 31, and is reflected by the first secondary reflection plane 31d to be made incident on the reflection plane 31c, and is totally reflected by the reflection plane 31c.

At the time of the total reflection by the reflection plane 31c, an evanescent component of the terahertz wave exists on a portion adjacent to the reflection plane 31c, of the subject S disposed on the reflection plane 31c. For this reason, the terahertz wave which has been totally reflected by the reflection plane 31c of the internal total reflection prism 31 acquires information on the portion adjacent to the reflection plane 31c, of the subject S. Then, the totally-reflected terahertz wave is reflected by the second secondary reflection plane 31e of the internal total reflection prism 31, to be output from the exit plane 31b, and the terahertz wave is, not propagated in a space, but directly received by the terahertz wave detecting element 40 provided so as to be integrated with the exit plane 31b of the internal total reflection prism 31.

On the other hand, the probe light L2 output from the branching part 12 is sequentially reflected by the mirrors M4 to M8 and the separator 17, to be received by the terahertz wave detecting element 40. The terahertz wave input from the separator 17 to the terahertz wave detecting element 40 passes through the terahertz wave detecting element 40, and thereafter, the terahertz wave is reflected by the exit plane 31b of the internal total reflection prism 31, and passes through the terahertz wave detecting element 40 again, to be output to the separator 17.

The terahertz wave and the probe light are received so as to be coaxial with each other by the terahertz wave detecting element 40 in substantially the same timing. In the terahertz wave detecting element 40 which receives the terahertz wave and the probe light, birefringence is induced in accordance with propagation of the terahertz wave, and a polarization state of the probe light is changed by the birefringence. The probe light output from the terahertz wave detecting element 40 to the separator 17 is transmitted through the separator 17. Then, the polarization state of the probe light is detected by the ¼ wavelength plate 51, the polarization split element 52, the photodetector 53A, the photodetector 53B, the differential amplifier 54, and the lock-in amplifier 55. In this way, the change in the polarization state of the probe light in the terahertz wave detecting element 40 is detected. As a result, an electric field amplitude of the terahertz wave is detected, which enables to acquire characteristics on the subject S.

Note that, by adjusting an optical path length between the mirrors M4 and M7 and the mirrors M5 and M6, and by adjusting an optical path length of the probe optical system in the optical path length difference adjusting part 14, a difference in respective timings of the terahertz wave and the probe light to be received by the terahertz wave detecting element 40 is adjusted. As described above, a pulse duration of a terahertz wave is generally approximately picoseconds, and in contrast thereto, a pulse duration of a probe light is approximately femtoseconds, that is, a pulse duration of a probe light is several digits narrower than that of a terahertz wave. For this reason, by sweeping the timing of incidence of the probe light to the terahertz wave detecting element 40 by the optical path length difference adjusting part 14, a temporal waveform of an electric field amplitude of the pulsed terahertz wave can be acquired.

As described above, the total reflection terahertz wave measuring apparatus 1 according to the first embodiment acquires information on the subject S disposed on the reflection plane 31c of the internal total reflection prism 31 with an evanescent component of a terahertz wave generated at the time of total reflection of the terahertz wave. Thereby, even in a case in which the subject S contains moisture, it is possible to measure the subject S easily and with high sensitivity. Further, because the terahertz wave generating element 20 and the terahertz wave detecting element 40 are provided so as to be integrated with the internal total reflection prism 31, it is easy to handle these, and from this standpoint as well, it is possible to measure the subject S easily, and it is possible to downsize the apparatus. Further, because the terahertz wave is, not propagated in a space, but propagated inside the internal total reflection prism 31 from the terahertz wave generating element 20 up to the terahertz wave detecting element 40, there is no need to conduct a nitrogen purge, and from this standpoint as well, it is possible to measure the subject S easily, and it is possible to downsize the apparatus. Moreover, because a loss of the terahertz wave through both of the entrance plane 31a and the exit plane 31b of the internal total reflection prism 31 is reduced, from this standpoint as well, it is possible to measure the subject S with high sensitivity.

SECOND EMBODIMENT

Figure 6:
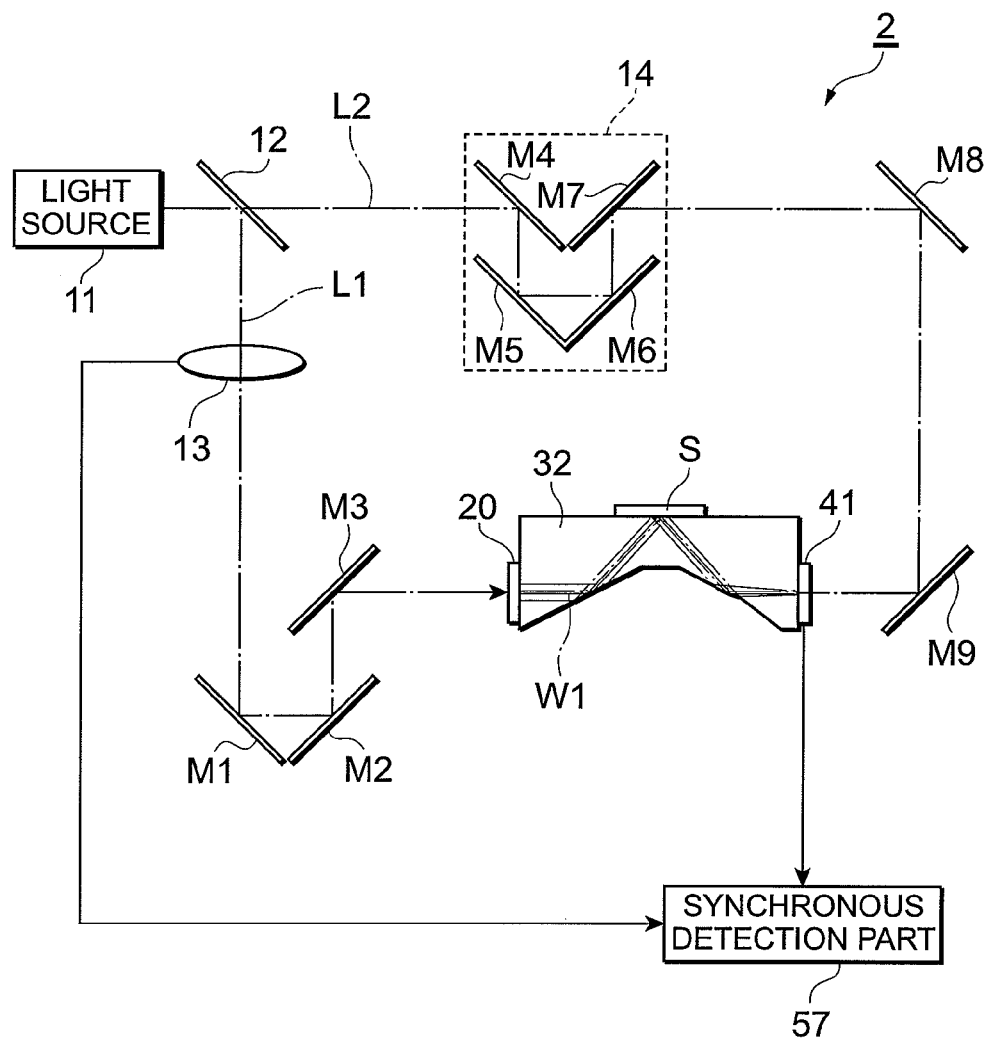
FIG. 6 is a diagram showing the configuration of a total reflection terahertz wave measuring apparatus 2 according to the second embodiment.

Next, a total reflection terahertz wave measuring apparatus 2 according to a second embodiment of the present invention will be described. FIG. 6 is a diagram showing the configuration of the total reflection terahertz wave measuring apparatus 2 according to the second embodiment. The total reflection terahertz wave measuring apparatus 2 shown in the drawing is configured to acquire information on the subject S by a total reflection measurement method by use of a terahertz wave, and the total reflection terahertz wave measuring apparatus 2 includes the light source 11, the branching part 12, the chopper 13, the optical path length difference adjusting part 14, the terahertz wave generating element 20, an internal total reflection prism 32, a terahertz wave detecting element 41, and a synchronous detection part 57.

Figure 7:
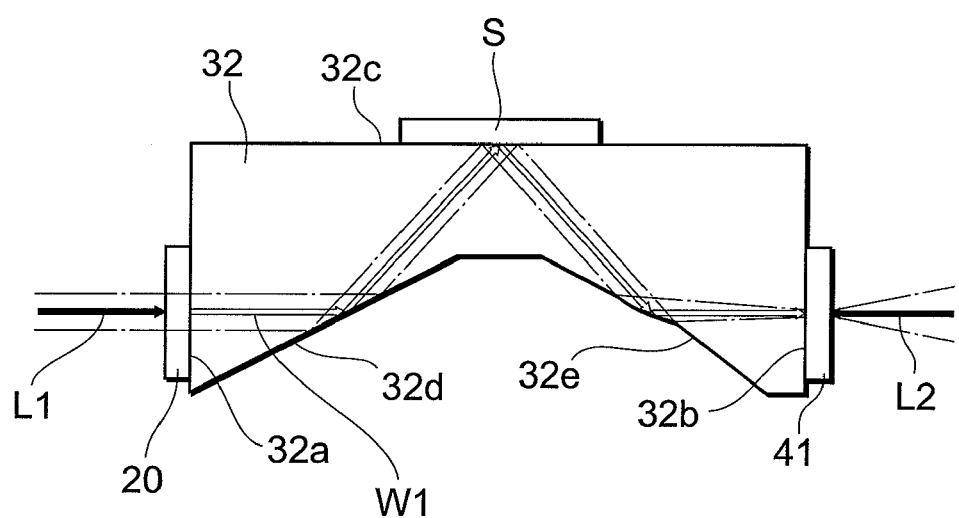
FIG. 7 is a cross sectional view of an internal total reflection prism 32 with which the terahertz wave generating element 20 and a terahertz wave detecting element 41 are provided to be integrated.

FIG. 7 is a cross sectional view of the internal total reflection prism 32 with which the terahertz wave generating element 20 and the terahertz wave detecting element 41 are provided to be integrated. The internal total reflection prism 32 is a so-called aplanatic prism, and has an entrance plane 32a, an exit plane 32b, a reflection plane 32c, a first secondary reflection plane 32d, and a second secondary reflection plane 32e. The entrance plane 32a and the exit plane 32b are parallel to one another. The reflection plane 32c is perpendicular to the entrance plane 32a and the exit plane 32b. The terahertz wave generating element 20 is provided to be integrated with the entrance plane 32a of the internal total reflection prism 32, and the terahertz wave detecting element 41 is provided to be integrated with the exit plane 32b of the internal total reflection prism 32.

Figure 8:
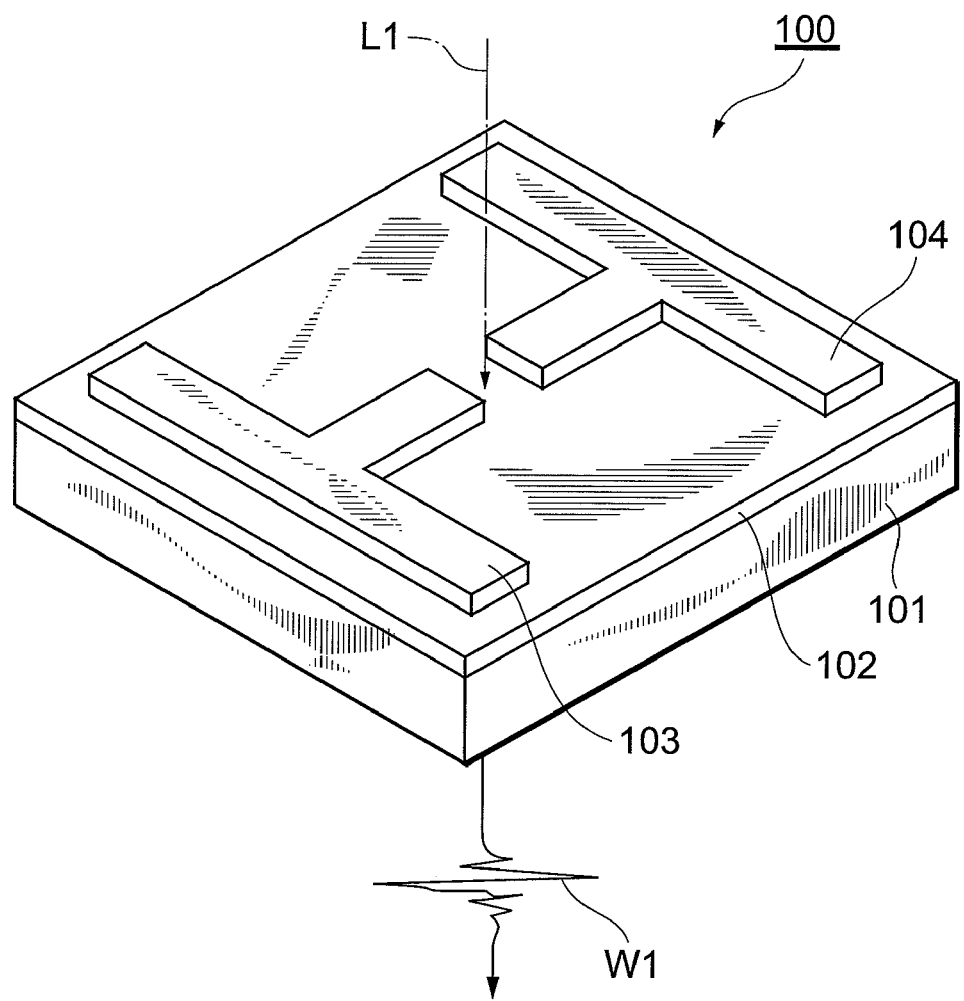
FIG. 8 is a perspective view of a photoconductive antenna element.

As the terahertz wave detecting element 41, a photoconductive antenna element as shown in FIG. 8 is used. The photoconductive antenna element 100 shown in FIG. 8 is used as the terahertz wave detecting element 41 or a terahertz wave generating element 21 which will be described later, and the photoconductive antenna element 100 has, for example, a semi-insulting GaAs substrate 101, a GaAs layer 102 formed on the GaAs substrate 101, and a pair of electrodes 103 and 104 formed on the GaAs layer 102. The GaAs layer 102 is epitaxial-grown at a low temperature (for example, 200 to 250° C. by MBE, and its thickness is, for example, 1 to 3 µm. The electrode 103 and the electrode 104 are ohmic electrodes of AuGe/Au or the like, and a length of an antenna thereof is, for example, 20 µm to 2 mm, and an interval between both electrodes is, for example, 3 to 10 µm. The GaAs layer 102 formed by low-temperature epitaxial growth is short in its carrier lifetime, high in its carrier mobility, and high in its impedance.

In the photoconductive antenna element 100 serving as the terahertz wave detecting element 41, in accordance with incidence of a terahertz wave and a probe light, an electric current indicating a correlation of both is generated between the electrode 103 and the electrode 104. A spectrum of the terahertz wave can be determined on the basis of the correlation, and moreover, information on a subject can be acquired. The electric current generated between the electrode 103 and the electrode 104 of the photoconductive antenna element 100 serving as the terahertz wave detecting element 41 is detected in synchronization with a period of generating a terahertz wave by the terahertz wave generating element 21 (i.e., a period at which the chopper 13 transmits a pump light) by the synchronous detection part 57.

Further, as shown in FIG. 7, a nonlinear optical crystal is provided as the terahertz wave generating element 20 integrally with the entrance plane 32a of the internal total reflection prism 32, and the photoconductive antenna element as described above is provided as the terahertz wave detecting element 41 integrally with the exit plane 32b of the internal total reflection prism 32. Accordingly, it is necessary to make a terahertz wave incident between the electrode 103 and the electrode 104 of the photoconductive antenna element as the terahertz wave detecting element 41. Then, an optical element yielding a light-condensing effect on a terahertz wave propagated inside the internal total reflection prism 32 is formed at the side of the exit plane 32b of the internal total reflection prism 32. That is, the second secondary reflection plane 32e has a shape of an off-axis paraboloidal mirror. Thereby, the terahertz wave totally reflected by the reflection plane 32c is reflected by the off-axis paraboloidal mirror serving as the second secondary reflection plane 32e, and is condensed to be made incident between the electrode 103 and the electrode 104 of the photoconductive antenna element serving as the terahertz wave detecting element 41 provided to the exit plane 32b.

The total reflection terahertz wave measuring apparatus 2 operates as follows. A pulsed light output from the light source 11 is branched into two to be the pump light L1 and the probe light L2 by the branching part 12. The pump light L1 output from the branching part 12 is sequentially reflected by the mirrors M1 to M3, to be received by the terahertz wave generating element 20 provided to be integrated with the entrance plane 32a of the internal total reflection prism 32. The terahertz wave generating element 20 generates and outputs the terahertz wave W1 in accordance with receiving the pump light L1. The terahertz wave W1 output from the terahertz wave generating element 20 is, not propagated in a space, but directly received by the entrance plane 32a of the internal total reflection prism 32, to be propagated inside the internal total reflection prism 32, and is reflected by the first secondary reflection plane 32d to be made incident on the reflection plane 32c, and is totally reflected by the reflection plane 32c.

At the time of the total reflection by the reflection plane 32c, an evanescent component of the terahertz wave exists on a portion adjacent to the reflection plane 32c, of the subject S disposed on the reflection plane 32c. For this reason, the terahertz wave which has been totally reflected by the reflection plane 32c of the internal total reflection prism 32 acquires information on the portion adjacent to the reflection plane 32c, of the subject S. Then, the totally-reflected terahertz wave is reflected by the off-axis paraboloidal mirror serving as the second secondary reflection plane 32e, to be output from the exit plane 32b of the internal total reflection prism 32, and the terahertz wave is, not propagated in a space, but directly received by the terahertz wave detecting element 41 provided to be integrated with the exit plane 32b of the internal total reflection prism 32.

The probe light which is output from the branching part 12, to be sequentially reflected by the mirrors M4 to M9 to reach the internal total reflection prism 32, is received between the electrode 103 and the electrode 104 of the photoconductive antenna element 100 serving as the terahertz wave detecting element 41. Further, the terahertz wave output from the exit plane 32b of the internal total reflection prism 32 as well, is received between the electrode 103 and the electrode 104 of the photoconductive antenna element 100 serving as the terahertz wave detecting element 41.

Because the pump light L1 is intermittently received by the terahertz wave generating element 20 at a constant period by the chopper 13, the terahertz wave W1 as well is intermittently generated at a constant period. In the photoconductive antenna element 100 serving as the terahertz wave detecting element 41, in accordance with incidence of a terahertz wave and a probe light, an electric current indicating a correlation of both is generated between the electrode 103 and the electrode 104. The electric current is detected in synchronization with a period at which the chopper 13 transmits a pump light by the synchronous detection part 57. Thereby, a spectrum of the terahertz wave can be determined, and moreover, information on the subject S can be acquired.

The total reflection terahertz wave measuring apparatus 2 according to the second embodiment is capable of yielding an advantageous effect, which is the same as the advantageous effect yielded by the total reflection terahertz wave measuring apparatus 1 according to the first embodiment.

THIRD EMBODIMENT

Figure 9:
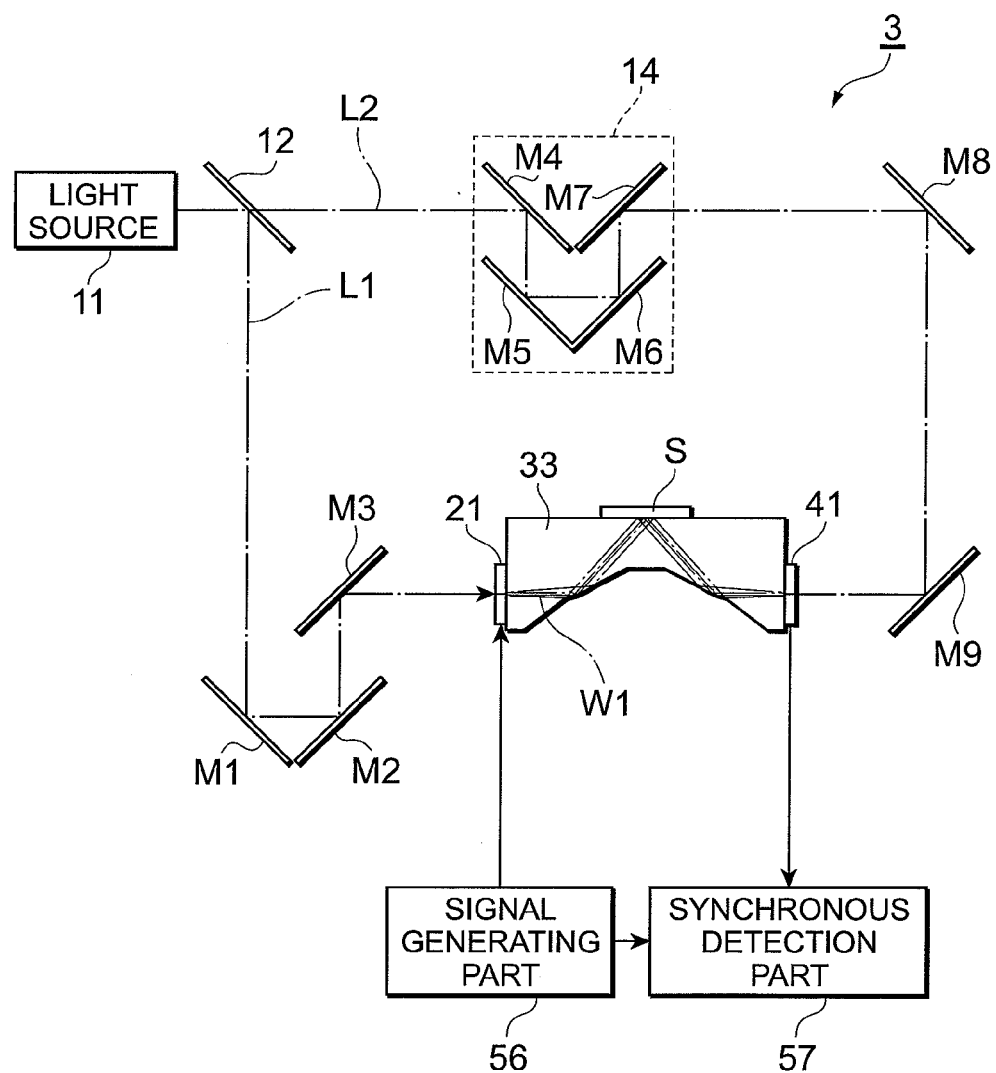
FIG. 9 is a diagram showing the configuration of a total reflection terahertz wave measuring apparatus 3 according to the third embodiment.

Next, a total reflection terahertz wave measuring apparatus 3 according to a third embodiment of the present invention will be described. FIG. 9 is a diagram showing the configuration of the total reflection terahertz wave measuring apparatus 3 according to the third embodiment. The total reflection terahertz wave measuring apparatus 3 shown in the drawing is configured to acquire information on the subject S by a total reflection measurement method by use of a terahertz wave, and the total reflection terahertz wave measuring apparatus 3 includes the light source 11, the branching part 12, the optical path length difference adjusting part 14, the terahertz wave generating element 21, an internal total reflection prism 33, the terahertz wave detecting element 41, a signal generating part 56, and the synchronous detection part 57.

Figure 10:
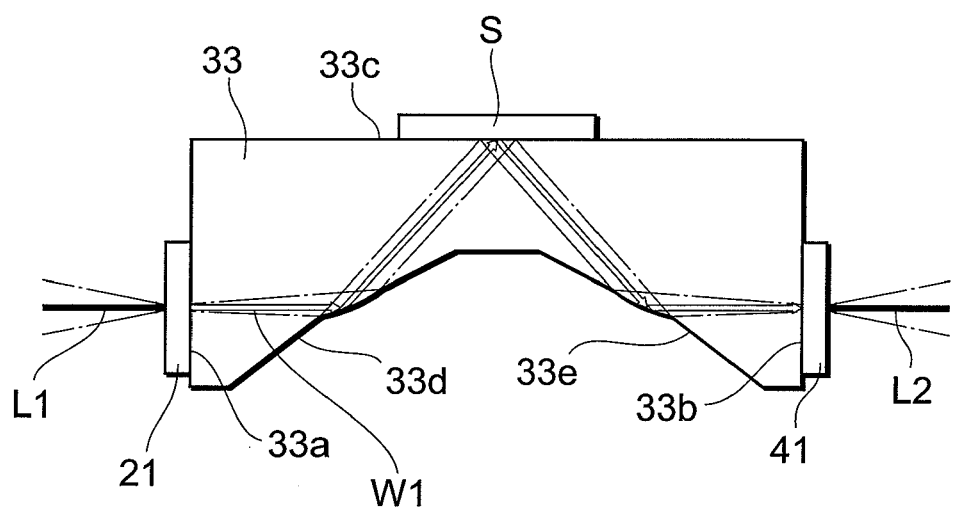
FIG. 10 is a cross sectional view of an internal total reflection prism 33 with which a terahertz wave generating element 21 and the terahertz wave detecting element 41 are provided to be integrated.

FIG. 10 is a cross sectional view of the internal total reflection prism 33 with which the terahertz wave generating element 21 and the terahertz wave detecting element 41 are provided to be integrated. The internal total reflection prism 33 is a so-called aplanatic prism, and has an entrance plane 33a, an exit plane 33b, a reflection plane 33c, a first secondary reflection plane 33d, and a second secondary reflection plane 33e. The entrance plane 33a and the exit plane 33b are parallel to one another. The reflection plane 33c is perpendicular to the entrance plane 33a and the exit plane 33b. The terahertz wave generating element 21 is provided to be integrated with the entrance plane 33a of the internal total reflection prism 33, and the terahertz wave detecting element 41 is provided to be integrated with the exit plane 33b of the internal total reflection prism 33.

As the terahertz wave generating element 21 and the terahertz wave detecting element 41 respectively, photoconductive antenna elements as shown in FIG. 8 are used. A voltage at a constant period is applied between the electrode 103 and the electrode 104 of the photoconductive antenna element 100 serving as the terahertz wave generating element 21 by the signal generating part 56. An electric current generated between the electrode 103 and the electrode 104 of the photoconductive antenna element 100 serving as the terahertz wave detecting element 41 is detected in synchronization with a period of generating a terahertz wave by the terahertz wave generating element 21 (i.e., a period of applying a voltage by the signal generating part 56) by the synchronous detection part 57.

Further, as shown in FIG. 10, the photoconductive antenna element is provided as the terahertz wave generating element 21 integrally with the entrance plane 33a of the internal total reflection prism 33, and the photoconductive antenna element is provided as the terahertz wave detecting element 41 integrally with the exit plane 33b of the internal total reflection prism 33. Accordingly, it is necessary to collimate the terahertz wave W1 generated to diffuse between the electrode 103 and the electrode 104 of the photoconductive antenna element serving as the terahertz wave generating element 21, and it is necessary to make a terahertz wave incident between the electrode 103 and the electrode 104 of the photoconductive antenna element serving as the terahertz wave detecting element 41.

Then, an optical element yielding a collimation effect on a terahertz wave propagated inside the internal total reflection prism 33 is formed at the side of the entrance plane 33a of the internal total reflection prism 33. Further an optical element yielding a light-condensing effect on a terahertz wave propagated inside the internal total reflection prism 33 is formed at the side of the exit plane 33b of the internal total reflection prism 33. That is, the first secondary reflection plane 33d and the second secondary reflection plane 33e respectively have shapes of off-axis paraboloidal mirrors. Thereby, a terahertz wave generated to diffuse between the electrode 103 and the electrode 104 of the photoconductive antenna element serving as the terahertz wave generating element 21, is reflected by the off-axis paraboloidal mirror serving as the first secondary reflection plane 33d to be collimated, and is made incident on the reflection plane 33c. Further, the terahertz wave totally reflected by the reflection plane 33c is reflected by the off-axis paraboloidal mirror serving as the second secondary reflection plane 33e, and is condensed to be made incident between the electrode 103 and the electrode 104 of the photoconductive antenna element serving as the terahertz wave detecting element 41.

The total reflection terahertz wave measuring apparatus 3 operates as follows. A pulsed light output from the light source 11 is branched into two to be the pump light L1 and the probe light L2 by the branching part 12. The pump light L1 output from the branching part 12 is sequentially reflected by the mirrors M1 to M3, to be received by the terahertz wave generating element 21 provided to be integrated with the entrance plane 33a of the internal total reflection prism 33. In the photoconductive antenna element 100 serving as the terahertz wave generating element 21, a voltage at a constant period is applied between the electrode 103 and the electrode 104 by the signal generating part 56, and the pump light L1 is received between the electrode 103 and the electrode 104, thereby generating the terahertz wave W1.

The terahertz wave W1 output from the terahertz wave generating element 21 is, not propagated in a space, but directly received by the entrance plane 33a of the internal total reflection prism 33, to be propagated inside the internal total reflection prism 33, and is reflected by the off-axis paraboloidal mirror serving as the first secondary reflection plane 33d to be collimated, and is made incident on the reflection plane 33c, and is totally reflected by the reflection plane 33c. At the time of the total reflection by the reflection plane 33c, an evanescent component of the terahertz wave exists on a portion adjacent to the reflection plane 33c, of the subject S disposed on the reflection plane 33c. For this reason, the terahertz wave which has been totally reflected by the reflection plane 33c of the internal total reflection prism 33 acquires information on the portion adjacent to the reflection plane 33c, of the subject S. Then, the totally-reflected terahertz wave is reflected by the off-axis paraboloidal mirror serving as the second secondary reflection plane 33e, to be output from the exit plane 33b of the internal total reflection prism 33, and the terahertz wave is, not propagated in a space, but directly received by the terahertz wave detecting element 41 provided to be integrated with the exit plane 33b of the internal total reflection prism 33.

The probe light which is output from the branching part 12 to be sequentially reflected by the mirrors M4 to M9 to reach the internal total reflection prism 33, is received between the electrode 103 and the electrode 104 of the photoconductive antenna element 100 serving as the terahertz wave detecting element 41. Further, the terahertz wave output from the exit plane 33b of the internal total reflection prism 33 as well, is received between the electrode 103 and the electrode 104 of the photoconductive antenna element 100 serving as the terahertz wave detecting element 41.

In the photoconductive antenna element 100 serving as the terahertz wave detecting element 41, an electric current indicating a correlation of both is generated between the electrode 103 and the electrode 104 in accordance with incidence of a terahertz wave and a probe light. The electric current is detected in synchronization with a period of applying a voltage by the signal generating part 56, by the synchronous detection part 57. Thereby, a spectrum of the terahertz wave can be determined, and moreover, information on the subject S can be acquired.

The total reflection terahertz wave measuring apparatus 3 according to the third embodiment is capable of yielding an advantageous effect which is the same as the advantageous effect yielded by the total reflection terahertz wave measuring apparatus 1 according to the first embodiment.

Note that, in the present embodiment, in a case in which a nonlinear optical crystal is provided as a terahertz wave generating element to be integrated with the entrance plane 33a of the internal total reflection prism 33, and the pump light L1 is condensed to irradiate the terahertz wave generating element, the terahertz wave W1 generated from the terahertz wave generating element diffuses. In such a case as well, it is preferable that an optical element yielding a collimation effect on a terahertz wave propagated inside the internal total reflection prism 33 is formed at the side of the entrance plane 33a of the internal total reflection prism 33.

MODIFICATION

Next, a modification of the total reflection terahertz wave measuring apparatus according to the present embodiment described above will be described. Hereinafter, a configuration of an internal total reflection prism with which a terahertz wave generating element and a terahertz wave detecting element are provided to be integrated, will be mainly described.

Figure 11:
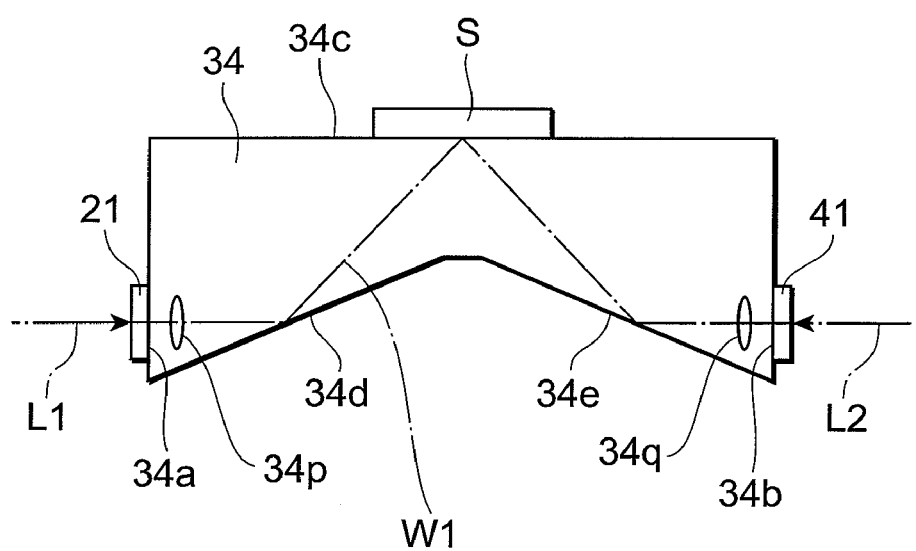
FIG. 11 is a cross sectional view of an internal total reflection prism 34 with which the terahertz wave generating element 21 and the terahertz wave detecting element 41 are provided to be integrated.

In the second and third embodiments, the optical elements for collimating or condensing a terahertz wave in the internal total reflection prism are composed of the off-axis paraboloidal mirrors formed on the first secondary reflection plane or the second reflection plane. In contrast thereto, an internal total reflection prism 34 shown in FIG. 11, an optical element for collimating a terahertz wave is composed of a lens 34p provided inside in the vicinity of an entrance plane 34a. Further an optical element for condensing a terahertz wave is composed of a lens 34q provided inside in the vicinity of an exit plane 34b.

The internal total reflection prism 34 directly receives the terahertz wave W1 generated by the terahertz wave generating element 21 on the entrance plane 34a, and collimates the terahertz wave propagated internally by the lens 34p, and makes the collimated terahertz wave to be sequentially reflected by a first secondary reflection plane 34d, a reflection plane 34c, and a second secondary reflection plane 34e, and condenses the terahertz wave by the lens 34q to output it from the exit plane 34b, and allows the terahertz wave to be directly received by the terahertz wave detecting element 41.

Figure 12:
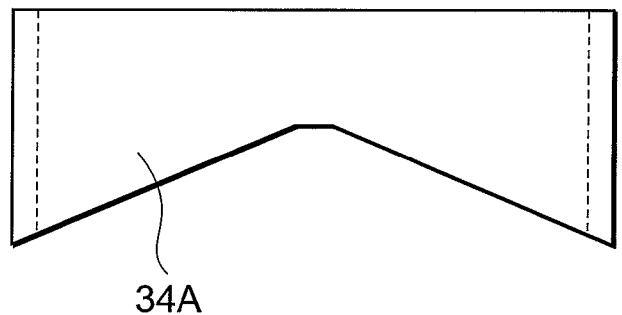
FIG. 12 are diagrams for describing a manufacturing process for the internal total reflection prism 34.
Figure 12:
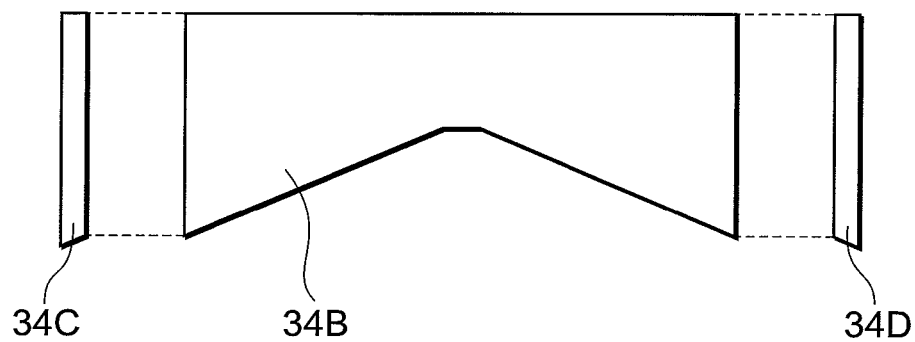
Figure 12:
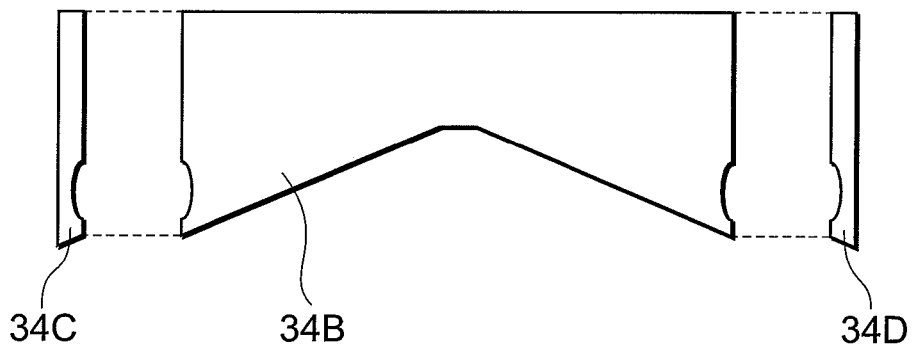

The internal total reflection prism 34 as described above can be manufactured through a process as described in FIG. 12. That is, a prism 34A having the same outline as the internal total reflection prism 34 is prepared (FIG. 12(a)), and the prism 34A is cut into members 34B, 34C, and 34D at the positions shown by the broken lines in the drawing (FIG. 12(b)). At this time, the cutting positions are the center lines of the positions at which the lenses 34p and 34q are to be provided. Next, recesses are formed in cutting planes at one sides of the members 34B, 34C, and 34D (FIG. 12(c)). Additionally, the recesses are filled with resin or powder, and the members 34B, 34C, and 34D are reconnected, to harden the resin or pack the powder. In this way, the internal total reflection prism 34 can be manufactured.

Note that, the shapes of the lenses 34p and 34q are dependent on a relationship between a refractive index of the resin with which the recesses are filled and a refractive index of the prism 34A. That is, when a refractive index of the resin is higher than that of the prism 34A at a terahertz wavelength, the shapes of the lenses 34p and 34q are to be convex lenses. Conversely, when a refractive index of the resin is lower than that of the prism 34A, the shapes of the lenses 34p and 34q are to be concave lenses. For example, the prism 34A is composed of silicon, and the resin with which the recesses are filled is composed of polyethylene.

In addition, a lens may be formed on the entrance plane or the exit plane of the internal total reflection prism. Further, a Fresnel lens may be formed internally or on the surface at a side of the entrance plane or the exit plane of the internal total reflection prism. In a case in which a Fresnel lens is formed internally, it is also possible to form the Fresnel lens by laser beam machining, and in the same way as the process described in FIG. 12, a prism may be cut, and a Fresnel lens may be formed in the cutting plane, and those may be reconnected. Provided that a lens is formed in this way, it is possible to collimate or condense a terahertz wave, and further, to transfer an image.

Further, in the above-described respective embodiments, the terahertz wave generating element and the terahertz wave detecting element are provided to be integrated with the internal total reflection prism. However, these are respectively separate members. In contrast thereto, an internal total reflection prism may be formed of GaAs, and a photoconductive antenna element serving as a terahertz wave generating element or a terahertz wave detecting element may be formed directly on the internal total reflection prism. Further, as shown in FIG. 13, a part of the internal total reflection prism may serve as a terahertz wave generating element as well, and another part of the internal total reflection prism may serve as a terahertz wave detecting element as well.

Figure 13:
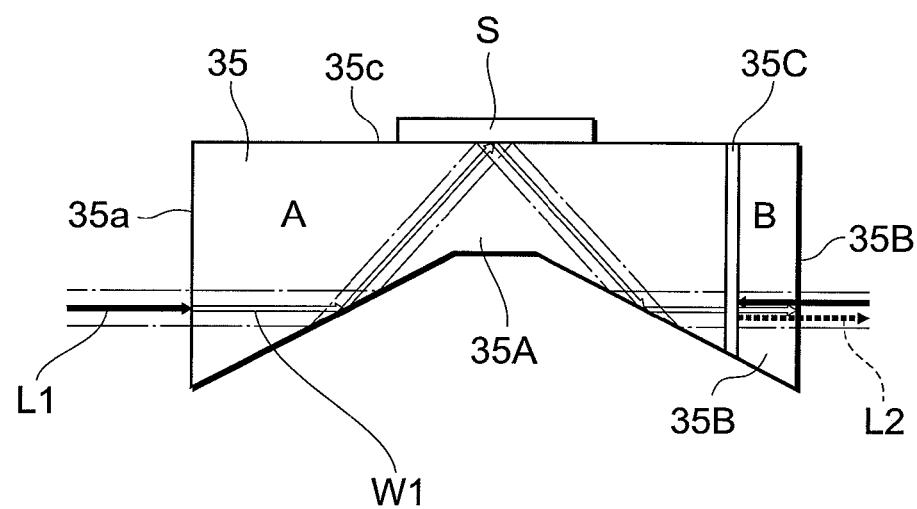
FIG. 13 is a cross sectional view of an internal total reflection prism 35 serving both as a terahertz wave generating element and a terahertz wave detecting element.

An internal total reflection prism 35 shown in FIG. 13 has the same outline as the internal total reflection prism 31 described above. However, a member 35A having an entrance plane 35a and a reflection plane 35c and a member 35B having an exit plane 35b are configured to sandwich a dielectric mirror 35C. The members 35A and 35B are composed of nonlinear optical crystals. The member 35A having the entrance plane 35a and the reflection plane 35c serves as a terahertz wave generating element as well, and has a crystal orientation in which it is possible to generate a terahertz wave W1. On the other hand, the member 35B having the exit plane 35b serves as a terahertz wave detecting element as well, and has a crystal orientation in which it is possible to detect a terahertz wave. The dielectric mirror 35C sandwiched between the member 35A and the member 35B is transmissive for a terahertz wave, and is capable of reflecting the probe light L2 with high efficiency. Further, an adhesive for connecting these is preferably transmissive for a terahertz wave. Additionally, its refractive index for a terahertz wave is preferably approximately the same as refractive indexes of the members 35A and 35B.

In the internal total reflection prism 35, the pump light L1 received by the entrance plane 35a is propagated inside the member 35A, and a terahertz wave W1 is generated during the propagation. The terahertz wave W1 is totally reflected by the reflection plane 35c, and thereafter, the terahertz wave W1 is transmitted through the dielectric mirror 35C to be received by the member 35B. On the other hand, the probe light L2 received by the exit plane 35b is propagated inside the member 35B to be reflected by the dielectric mirror 35C, and is propagated inside the member 35B again to be output from the exit plane 35b. In the member 35B, birefringence is induced due to a Pockels effect in accordance with propagation of the terahertz wave, and a polarization state of the probe light is changed by the birefringence. Because an amount of birefringence at this time is dependent on an electric field intensity of the terahertz wave, an amount of change in the polarization state of the probe light in the terahertz wave detecting element is dependent on an electric field intensity of the terahertz wave.

In this way, in the configuration of the internal total reflection prism 35 shown in FIG. 13, it is possible to further downsize the apparatus, and handling thereof is easy.

Figure 14:
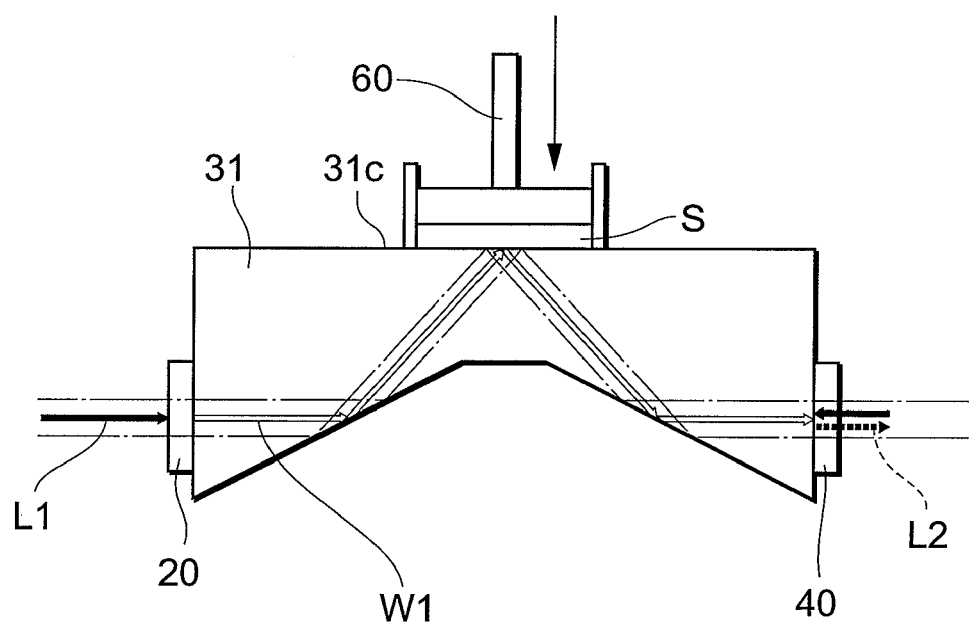
FIG. 14 is a diagram for describing a mechanism 60 that presses a subject S against a reflection plane 31c of the internal total reflection prism 31.

Further, in a case in which the subject S disposed on the reflection plane 31c of the internal total reflection prism 31 is powder, as shown in FIG. 14, a mechanism 60 that presses the subject S against the reflection plane 31c of the internal total reflection prism 31 is preferably provided. By pressing the subject S against the reflection plane 31c by the presser mechanism 60, the subject S is adhered more tightly to the reflection plane 31c, which makes it possible to efficiently perform total reflection measurement.

The invention claimed is:

1. A total reflection terahertz wave measuring apparatus comprising:
   a light source for outputting light;
   a branching part for branching the light output from the light source into two, to output one of the lights branched into two as a pump light and the other one as a probe light;
   a terahertz wave generating element for generating and outputting a terahertz wave by receiving the pump light output from the branching part;
   an internal total reflection prism for receiving the terahertz wave output from the terahertz wave generating element on an entrance plane, making the received terahertz wave be propagated internally to be totally reflected by a reflection plane, and outputting the terahertz wave from an exit plane to the outside; and
   a terahertz wave detecting element for receiving the terahertz wave output from the exit plane of the internal total reflection prism and the probe light output from the branching part, to detect a correlation between the terahertz wave and the probe light,
   wherein the terahertz wave generating element is provided to be integrated with the entrance plane of the internal total reflection prism,
   wherein the terahertz wave detecting element is provided to be integrated with the exit plane of the internal total reflection prism,
   wherein the internal total reflection prism has, in addition to the entrance plane, the reflection plane, and the exit plane, a first secondary reflection plane for reflecting the terahertz wave received by the entrance plane to be propagated internally toward the reflection plane, and a second secondary reflection plane for reflecting the terahertz wave reflected by the reflection plane to be propagated internally toward the exit plane,
   wherein the first secondary reflection plane is provided to yield a collimation effect on the terahertz wave received by the entrance plane to be propagated inside the internal total reflection prism, and
   wherein information on a subject disposed on the reflection plane of the internal total reflection prism is acquired with an evanescent component of the terahertz wave generated at the time of total reflection of the terahertz wave.

2. The total reflection terahertz wave measuring apparatus according to claim 1, further comprising
an optical path length difference adjusting part for adjusting a difference between an optical path of the pump light and the terahertz wave from the branching part up to the terahertz wave detecting element and an optical path of the probe light from the branching part up to the terahertz wave detecting element.

3. The total reflection terahertz wave measuring apparatus according to claim 1, wherein
a principal ray of the terahertz wave received by the entrance plane of the internal total reflection prism and a principal ray of the terahertz wave output from the exit plane of the internal total reflection prism are on a common straight line.

4. A total reflection terahertz wave measuring apparatus comprising:
a light source for outputting light;
a branching part for branching the light output from the light source into two, to output one of the lights branched into two as a pump light and the other one as a probe light;
a terahertz wave generating element for generating and outputting a terahertz wave by receiving the pump light output from the branching part;
an internal total reflection prism for receiving the terahertz wave output from the terahertz wave generating element on an entrance plane, making the received terahertz wave be propagated internally to be totally reflected by a reflection plane, and outputting the terahertz wave from an exit plane to the outside; and
a terahertz wave detecting element for receiving the terahertz wave output from the exit plane of the internal total reflection prism and the probe light output from the branching part, to detect a correlation between the terahertz wave and probe light,
wherein the terahertz wave generating element is provided to be integrated with the entrance plane of the internal total reflection prism,
wherein the terahertz wave detecting element is provided to be integrated with the exit plane of the internal total reflection prism,
wherein the internal total reflection prism has, in addition to the entrance plane, the reflection plane, and the exit plane, a first secondary reflection plane for reflecting the terahertz wave received by the entrance plane to be propagated internally toward the reflection plane, and a second secondary reflection plane for reflecting the terahertz wave reflected by reflection plane to be propagated internally toward the exit plane,
wherein the second secondary reflection plane is provided to yield a light condensing effect on the terahertz wave reflected by the reflection plane to be propagated inside the internal total reflection prism, and
wherein information on a subject disposed on the reflection plane of the internal total reflection prism is acquired with an evanescent component of the terahertz wave generated at the time of total reflection of the terahertz wave.

5. The total reflection terahertz wave measuring apparatus according to claim 4, further comprising:
an optical path length difference adjusting part for adjusting a difference between an optical path of the pump light and the terahertz wave from the branching part up to the terahertz wave detecting element and an optical path of the probe light from the branching part up to the terahertz wave detecting element.

6. The total reflection terahertz wave measuring apparatus according to claim 4, wherein
a principal ray of the terahertz wave received by the entrance plane of the internal total reflection prism and a principal ray of the terahertz wave output from the exit plane of the internal total reflection prism are on a common straight line.

* * * * *

UNITED STATES PATENT AND TRADEMARK OFFICE
CERTIFICATE OF CORRECTION

PATENT NO. : 8,354,644 B2
APPLICATION NO. : 12/530897
DATED : January 15, 2013
INVENTOR(S) : Yasuda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 650 days.

Signed and Sealed this
First Day of September, 2015

Michelle K. Lee
*Director of the United States Patent and Trademark Office*